(12) United States Patent (10) Patent No.: US 9,138,593 B2
Surrenti et al. (45) Date of Patent: Sep. 22, 2015

(54) **INGESTIBLE CAPSULE FOR TREATING GASTRIC INFECTIONS, IN PARTICULAR FOR TREATING *H. PYLORI* INFECTIONS**

(75) Inventors: Calogero Surrenti, Bagno a Ripoli (IT); Franco Fusi, Pontassieve (IT); Elisabetta Surrenti, Florence (IT); Giovanni Romano, Florence (IT); Barbara Orsini, Florence (IT); Monica Monici, Florence (IT)

(73) Assignee: UNIVERSITA' DEGLI STUDI DI FIRENZE, Florence (IT)

( * ) Notice: Subject to any disclaimer, the term of this patent is extended or adjusted under 35 U.S.C. 154(b) by 195 days.

(21) Appl. No.: 13/508,195

(22) PCT Filed: Nov. 6, 2009

(86) PCT No.: PCT/IT2009/000499
§ 371 (c)(1),
(2), (4) Date: May 4, 2012

(87) PCT Pub. No.: WO2011/055395
PCT Pub. Date: May 12, 2011

(65) Prior Publication Data
US 2012/0226335 A1 Sep. 6, 2012

(51) Int. Cl.
*A61N 5/067* (2006.01)
*A61N 5/06* (2006.01)

(52) U.S. Cl.
CPC ............ *A61N 5/0603* (2013.01); *A61N 5/0624* (2013.01); *A61N 5/0601* (2013.01);
(Continued)

(58) Field of Classification Search
CPC .............. A61B 1/04; A61B 1/06; A61B 5/00; A61B 8/00; A61B 17/00; A61B 18/04; A61B 17/24; A61B 11/00; A61H 21/00; A61M 31/00; A61K 9/14; H01M 4/13; H01H 3/12; G02B 21/18; G02B 17/00; G08B 5/22
USPC ......... 600/109, 160, 176–179, 309–310, 437, 600/175; 606/1, 32, 161, 162; 607/86; 604/65; 424/488; 429/229; 200/412; 348/76; 359/372, 736; 340/815.45
See application file for complete search history.

(56) References Cited

U.S. PATENT DOCUMENTS 4,712,889 A * 12/1987 Schindl .......................... 359/372
5,604,531 A * 2/1997 Iddan et al. ...................... 348/76
(Continued)

FOREIGN PATENT DOCUMENTS

EP 1714607 10/2006
JP 2003210395 7/2003
(Continued)

OTHER PUBLICATIONS

Hamblin et al; *Helicobacter pylori* Accumulates Photoactive Porphyrins and Is Killed by Visible Light; Antimicrobial Agents and Chemotherapy; vol. 49, No. 7; Jul. 2005, p. 2822-2827.
(Continued)

*Primary Examiner* — Gary Jackson
*Assistant Examiner* — Victor Shapiro
(74) *Attorney, Agent, or Firm* — Abelman, Frayne & Schwab

(57) ABSTRACT

The light capsule object of the present invention is an ingestible device designed to illuminate the gastric cavity of the stomach for therapeutic purposes directed against *Helicobacter pylori* (*H. pylori*) bacteria. It comprises: a casing transparent to visible light, in turn containing punctiform light sources, preferably constituted by LEDs, positioned immediately under said casing and capable of emitting light at appropriate wavelength bands (preferably 405 nm and 630 nm); a battery, adapted to power the LED sources for approximately 20-30 minutes (the average transit time in the stomach); a switch which allows a delayed power on and allows the tablet to be still "off" when it is swallowed. The light emitted by the capsule strikes the *H. pylori* bacteria anchored on the gastric wall. The light radiation is preferentially absorbed by molecules of porphyrin produced by the bacterium which works as photosensitizing agent by inducing the formation of cytotoxic molecular species.

15 Claims, 1 Drawing Sheet

(52) U.S. Cl.
CPC .......... *A61N 5/062* (2013.01); *A61N 2005/067* (2013.01); *A61N 2005/0609* (2013.01); *A61N 2005/0651* (2013.01); *A61N 2005/0653* (2013.01); *A61N 2005/0662* (2013.01)

(56) References Cited

U.S. PATENT DOCUMENTS

| | | | |
|---|---|---|---|
| 5,838,247 A * | 11/1998 | Bladowski | 340/815.45 |
| 6,187,021 B1 * | 2/2001 | Wim | 606/162 |
| 6,855,111 B2 * | 2/2005 | Yokoi et al. | 600/179 |
| 6,998,555 B2 * | 2/2006 | Collot et al. | 200/412 |
| 7,929,219 B2 * | 4/2011 | Togino | 359/736 |
| 8,515,507 B2 * | 8/2013 | Rabinovitz et al. | 600/310 |
| 2001/0051766 A1 * | 12/2001 | Gazdzinski | 600/309 |
| 2004/0039242 A1 | 2/2004 | Tolkoff et al. | |
| 2005/0069589 A1 * | 3/2005 | Lowinger et al. | 424/488 |
| 2005/0137468 A1 * | 6/2005 | Avron et al. | 600/310 |
| 2005/0192478 A1 | 9/2005 | Williams et al. | |
| 2006/0082648 A1 * | 4/2006 | Iddan et al. | 348/76 |
| 2006/0167531 A1 * | 7/2006 | Gertner et al. | 607/86 |
| 2008/0039768 A1 | 2/2008 | Francis | |
| 2008/0045797 A1 * | 2/2008 | Yasushi et al. | 600/175 |
| 2009/0137876 A1 | 5/2009 | Brophy | |
| 2009/0142667 A1 * | 6/2009 | Ryou | 429/229 |
| 2009/0177033 A1 * | 7/2009 | Hendriks et al. | 600/109 |
| 2012/0136209 A1 * | 5/2012 | Kostenich et al. | 600/109 |

FOREIGN PATENT DOCUMENTS

| | | | |
|---|---|---|---|
| WO | WO2008012701 | 1/2008 | |
| WO | WO2008157711 | * 12/2008 | C08F 2/18 |

OTHER PUBLICATIONS

Written Opinion and ISR for International Application No. PCT/IT2009/000499 dated May 3, 2010.

* cited by examiner

INGESTIBLE CAPSULE FOR TREATING GASTRIC INFECTIONS, IN PARTICULAR FOR TREATING *H. PYLORI* INFECTIONS

CROSS-REFERENCE TO RELATED APPLICATIONS

This application is a National Phase of PCT/IT2009/000499, filed on Nov. 6, 2009, said application being incorporated herein by reference.

FIELD OF THE INVENTION

The present invention relates to the field of devices for the therapeutic treatment of patients, and in particular to the field of devices for treating *H. pylori* infections.

STATE OF THE ART

As known, *H. pylori* is a bacterium considered one of the causing agents of inflammation and ulcerous lesions of the stomach and duodenum; in particular, infection by this bacterium is associated to chronic gastritis, gastro-duodenal ulcer, cancer and gastric lymphoma.

*H. pylori* infection is treated by using a pharmacological eradication therapy, generally consisting of the association of an antisecretion drug and two and/or three antibiotics. M. R. Hamblin et al. announced in "Antimicrobial Agents and Chemotherapy", July 2005, p. 2822-2827, that *H. pylori* is sensitive to the action of visible light and suggested the use of photodynamic therapy for in vivo treatment of infected patients.

Apparatuses consisting of capsules capable of illuminating internal organs for diagnostic purposes are known, such as for example from patent U.S. 2007/0238921, but the devices of the prior art do not contemplate the possibility of providing targeted lighting for the treatment of *H. pylori* bacteria colonies.

Indeed, in the aforesaid patent, the light source provided to the device is optimized in terms of wavelength and intensity to promote the energizing of exogenous fluorophores (e.g. quantum dots), thus being inappropriate for therapeutic use aimed at energizing endogenous molecules, such as porphyrins. Lighting is highly directional, and thus only illuminates a very limited portion of the gastric mucous membrane; the presence of the camera and transmitter is unnecessary for the purposes of the present invention, in addition to consuming energy which could otherwise be used for energizing the porphyrins. Furthermore, the light energy used to energize fluorescence is much lower than that needed for obtaining a photodynamic effect, as in this case.

It would thus be extremely useful to have a device capable of radiating high-intensity light at an appropriate wavelength onto the stomach walls colonized by *H. pylori* bacterium so as to prevent proliferation and thus promote elimination.

DISCLOSURE OF THE INVENTION

An ingestible device for illuminating the gastric cavity of the stomach for therapeutic purposes comprising: an external casing 1; at least one punctiform light source; a battery 3; a power supply circuit associated to said battery and to said at least one punctiform light source; a switch 10 associated to said power supply source; at least one semi-reflecting mirror 8 associated to said at least one punctiform light source and adapted to produce a light emission extended over most of the solid angle, said outer casing 1 being transparent to radiation emitted by said at least one punctiform light source and made of non-digestible material.

DETAILED DESCRIPTION OF THE INVENTION

The present invention allows to overcome the above-described problems by means of an ingestible capsule provided with lighting means adapted to illuminate the desired organ (in this case, the stomach and the duodenum).

The purpose of the capsule is to provide high-intensity light as uniform as possible for photo-therapeutic purposes.

Figure 1:
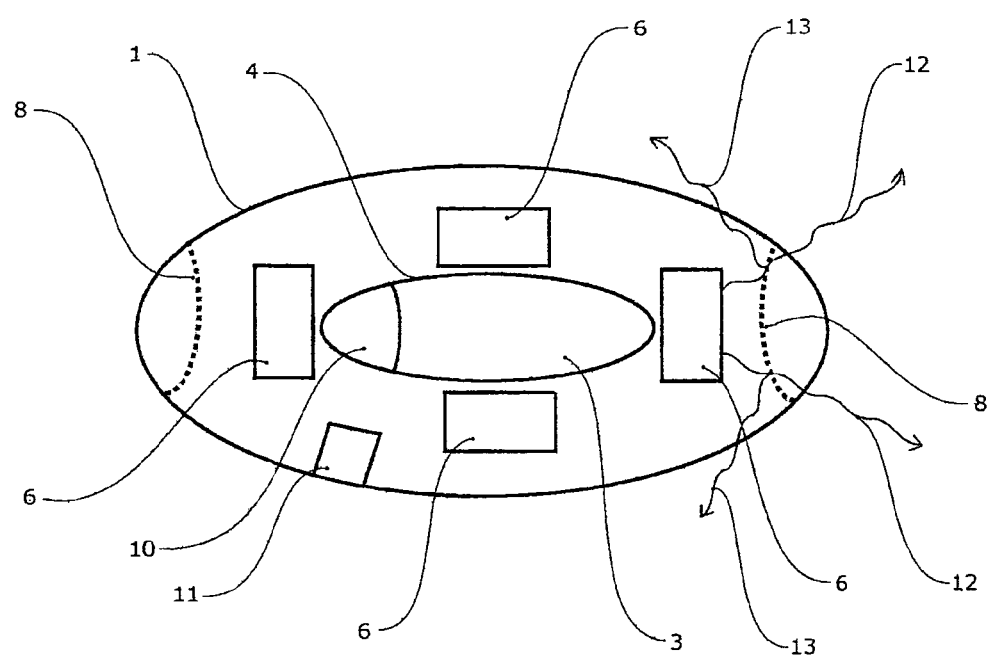
FIG. 1 shows a diagram of an inner structure of a first preferred embodiment of the device according to the present invention.
Figure 2:
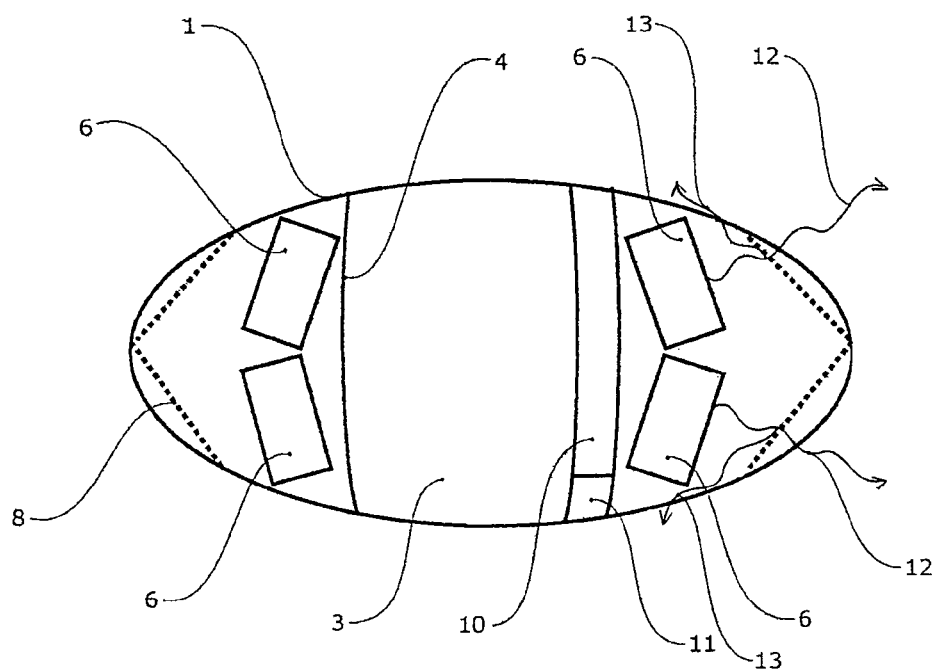
FIG. 2 shows a diagram of the inner structure of a second preferred embodiment of the device according to the present invention.

With reference to FIG. 1, the device object of the present invention comprises:
- an external casing 1;
- a battery 3;
- at least one punctiform light source, preferably consisting of a LED 6;
- a power supply circuit associated to said battery and to said at least one punctiform light source;
- at least one semi-reflecting mirror 8 associated to said at least one punctiform light source and adapted to promote a light emission extended over most of the solid angle;
- a switch 10 associated to said power supply circuit.

In further detail, said external casing 1 is transparent to radiation emitted by said at least one punctiform light source and is made of non-digestible material, e.g. polymethyl methacrylate (PMMA), adapted to promote the adhesion thereof onto the stomach wall and preferably coated with a layer of slippery material adapted to promote the its swallowing and be rapidly dissolved by gastric acid. Said outer casing 1 may further be adapted to contain a mixture of air enriched with oxygen at pressure higher than atmospheric pressure so as to optimize the operation of said battery 3.

Said at least one light source is of the type adapted to emit appropriate wavelengths, preferably 405 nm and 630 nm; furthermore, it comprises at least one high-intensity LED positioned immediately underneath said transparent casing 1 and about the battery 3 from which they take the required power. Said battery 3 should contain sufficient energy for powering the LEDs for at least 20-30 minutes (the average transit time in the gastric antrum).

Said switch 10, associated to said battery 3, is preferably timed 10, so as to allow a delayed lighting and allow the tablet to be still "off" when it is swallowed and turned on later. Said ignition should preferably occur within a time either comparable to or lower than the average time required by the capsule to reach the stomach (e.g. 10-60 seconds).

Given the optimal geometric configuration for promoting swallowing (cylindrical shape of the capsule with rounded side surfaces), the battery will be positioned in the middle with the LEDs around it. Appropriately shaped semi-transparent (reflecting) mirrors 8 will be inserted within said capsule in order to improve radiation. In this manner, the wavelengths of the reflected light 13 are the same as those of the light 12 which directly crosses the reflectors.

In a preferred embodiment of the present invention, said capsule is made in oxygen enriched atmosphere, and possibly with inner pressure higher than atmospheric pressure to allow use of a zinc-air battery. For this purpose, the battery may be provided with an appropriate casing 4 containing compressed air and such to guarantee optimal operating conditions, in addition to preventing the release of gas contained therein. The zinc-air battery is indeed today one with the highest KWh/m$^3$ ratio with regards to the delivered energy per unit of volume of the battery.

Alternatively to zinc-air batteries, other types of batteries may be used, e.g. lithium type batteries.

The light transmitted by LED sources is in part transmitted 12 by the semi-transparent mirrors 8 and in part reflected 13, thus crosses the casing of the capsule 1 and strikes the target constituted by the *H. pylori* bacterium.

Within the bacterium struck by light radiation emitted by the capsule according to the present invention, the light is in particular absorbed by the present porphyrin molecules, thus performing the desired therapeutic action.

The external sizes of the capsule according to the present invention are such to easily pass through the entire digestive tract, and will be preferably coated with a biocompatible substance also having a sealing function so as to prevent the release of potentially toxic substances contained within the capsule. Preferably, the capsule according to the present invention will have a diameter smaller than or equal to 12 mm and a length smaller than or equal to 26 mm.

Plastic material coating is preferred, providing that it is transparent to the radiation emitted by the light sources within the capsule itself. If preferred, said coating will be chosen from the materials having diffusive light emission features, according to an emission as distributed as possible across the entire solid angle and not directly outwards in few, very precise directions. The purpose is indeed to be able to invest most surface of the inner wall of the stomach with light.

Furthermore, the coating, considering the requirements of non-toxicity, may be made so as to promote swallowing but at the same time loose this feature of "slipperiness" as soon as it reaches the stomach.

Preferably, the capsule will be provided with an outer coating (which is eliminated by contact with the liquid physiologically present in the gastric lumen) making it slippery and easy to swallow and with an inner coating which instead promotes adhesion onto the walls of the stomach.

For example, in order to obtain optimal capsule positioning and lighting conditions, the therapeutic treatment may be preceded by ingesting a specific powder and water which leads to the rapid formation of a gel; such a gel has the purpose of promoting distension of the stomach and slowing down the capsule in the gastric lumen. The capsule is swallowed immediately after administration of the gel (1-2 minutes). The gel which must be transparent to the light emitted by the capsule has the further purpose of scattering the emitted light so as to illuminate the widest surface possible.

The capsule according to the invention is adapted to emit visible light radiation with emission spectrum characterized by either one or two peaks, i.e. by a one-color emission (red or violet) or by a two-color emission (red and violet) at the same time.

This need is related to that fact that red light has a better penetration in tissues but less bactericide efficiency, while violet light on the other hand has a lower penetration but a better cytotoxic efficacy.

Punctiform light sources preferably used in the device according to the present invention consist of LED, OLED or laser diodes. Laser diodes have higher efficiency but offer unnecessary performances for the purpose of the present invention, performances which may have negative effect on the costs of the device. Furthermore, laser diodes have a much more directed emission and thus unfavorable for the purpose of the present invention. OLEDs are very promising light energy sources, although they are now intrinsically not very bright, i.e. the density of light energy emitted per solid angle unit is very low, and currently with efficiency lower than that of LEDs.

The emitted spectrum will have emission peak spectrum width about 20 nm (FWHM) and an emission wavelength centered in red of about 650 nm and in violet of about 405 nm.

The light emission lobe must be extended across the widest possible solid angle so as to allow a poorly directed emission. LEDs (both single and in form of LED arrays) with an emission lobe which ranges from +/−30 degrees to +/−60 degrees exist on the market for this purpose.

In order to obtain the desired light emission, several LED sources appropriately arranged in the capsule must be used, so as to partially overlap the emission lobes and cover the widest possible solid angle.

The emitted light intensity (Watt/cm$^2$) must be as high as possible, compatibly with non-dangerous levels for healthy tissue; the total energy emitted on the solid global emission angle, during the illumination time, should be such to perform an effective cytotoxic action (e.g. values of 30 J/cm$^2$).

The light source of the device according to the present invention must be turned on immediately after ingestion by activating said switch 10, associated to said battery 3, e.g. by using a miniature switch 11 actuatable by means of pressure on the outer surface of the capsule or simply by screwing the two half-portions of the capsule. Alternatively, in a further preferred embodiment of the present invention, the capsule may be turned on from the outside, e.g. by means of appropriate reception means included in the capsule and adapted to pick up a remote power-on signal. In order to implement the aforesaid functions, the capsule should be provided with a specific electronic circuitry arranged inside it and provided with the following features: having low power consumption, being such circuitry powered by the battery inside the capsule; having lower heat dispersion, so as not to cause potential damage to the tissues and to the capsule itself; and being as miniaturized as possible.

The capsule may be further equipped with a sensor for signally entrance into the intestine and either switch it off or be provided with a remote power-off system similar to that described above with regards to power-on.

Due to heat dispersion of part of the energy used by the LEDs (and by the circuitry integrated in the tablet itself), it may be necessary to provide the tablet with a heat sink system. The latter, preferably of passive type, has the purpose of decreasing the temperature of the tablet so as to make it as uniform with the surrounding ambient temperature (stomach cavity, intestine) as possible.

In order to release light energy for eliminating the highest possible number of bacteria (*H. pylori*), several tablets may be swallowed in time or the treatment may be extended in time (e.g. over 1-2 weeks).

Furthermore, preferably, before swallowing the device, a gelatinous substance mixed with water and transparent to the radiation emitted by the capsule may be introduced into the patient's stomach, for the purpose of distending the plicae gastricae, thus favoring uniformity of illumination and efficacy of the illuminating capsule according to the present invention.

The invention claimed is:

1. An ingestible untethered device for illuminating the gastric cavity of the stomach for therapeutic purposes comprising: an external casing; at least one punctiform light source, said external casing being transparent to radiation emitted by said at least one punctiform light source and made of non-digestible material; a battery; a power supply circuit associated to said battery and to said at least one punctiform light source; a switch associated to said power supply source characterized in that it comprises at least one internal semi-reflecting mirror associated to said at least one punctiform light source and adapted to produce a diffused light emission directed outside said external casing across the entire solid angle.

2. The device according to claim 1, wherein said outer casing is coated by a surface layer of slippery material adapted to be rapidly dissolved by gastric liquids.

3. The device according to claim 1, wherein said outer casing is further adapted to contain a mixture of air enriched with oxygen.

4. The device according to claim 2, comprising a further coating layer, underneath said slippery material surface layer and adapted to adhere to the stomach wall.

5. The device according to claim 1, wherein said at least one punctiform light source is of the type adapted to emit appropriate wavelength bands comprising values of 405 nm and 630 nm.

6. The device according to claim 1, wherein said at least one punctiform light source is such to emit a emission lobe of width comprised from +/−30 degrees to +/−60 degrees.

7. The device according to claim 1, wherein said at least one punctiform light source is chosen from the group comprising LEDs, OLEDs and laser diodes.

8. The device according to claim 1, wherein said outer casing is made of polymethyl methacrylate (PMMA).

9. The device according to claim 1, wherein battery is of the lithium type.

10. The device according to claim 1, wherein said battery is of the zinc-air type.

11. The device according to claim 10, wherein said battery is provided with an appropriate casing adapted to contain air enriched with oxygen.

12. The device according to claim 10, wherein said switch, associated to said battery, is further associated to a miniaturized switch operatable by means of pressure on the outer surface of said device or by means of simple screwing of two semi-portions of said device.

13. The device according to claim 10, wherein said switch is a timed switch so as to allow a delayed power-on to allow said device to be swallowed still off and turned on later.

14. The device according to claim 10, wherein said switch can be remotely operated.

15. The device according to claim 10, having a diameter equal to or smaller than 12 mm and by a length shorter than or equal to 26 mm.

* * * * *